(12) United States Patent
Sherrill et al.

(10) Patent No.: US 7,091,193 B2
(45) Date of Patent: Aug. 15, 2006

(54) THERAPEUTIC FORMULATIONS

(75) Inventors: Michael J. Sherrill, Danville, CA (US);
Robert G. Johnson, Jr., Lafayette, CA (US)

(73) Assignee: Kosan biosciences Incorporated, Hayward, CA (US)

(*) Notice: Subject to any disclaimer, the term of this patent is extended or adjusted under 35 U.S.C. 154(b) by 0 days.

(21) Appl. No.: 10/683,952

(22) Filed: Oct. 9, 2003

(65) Prior Publication Data

US 2004/0132692 A1 Jul. 8, 2004

Related U.S. Application Data

(60) Provisional application No. 60/426,585, filed on Nov. 14, 2002, provisional application No. 60/417,536, filed on Oct. 9, 2002.

(51) Int. Cl.
*A61K 31/724* (2006.01)
*A61K 31/715* (2006.01)
*C08B 37/16* (2006.01)

(52) U.S. Cl. .................. 514/58; 514/365; 536/103
(58) Field of Classification Search .................. 514/58, 514/365, 46; 536/103, 46
See application file for complete search history.

(56) References Cited

U.S. PATENT DOCUMENTS 6,194,181 B1 * 2/2001 Hofmann et al. ........... 435/118

| 6,380,227 | B1 | 4/2002 | Mutz |
| 6,380,395 | B1 | 4/2002 | Vite et al. |
| 6,683,100 | B1 * | 1/2004 | van Hoogevest ........... 514/365 |
| 2005/0148543 | A1 | 7/2005 | Sherrill et al. |

FOREIGN PATENT DOCUMENTS

| WO | WO 99/39694 A2 | 8/1999 |
| WO | WO 99/42602 | 9/1999 |
| WO | WO 02/066033 A1 | 8/2002 |
| WO | WO 02/066038 A1 | 8/2002 |

OTHER PUBLICATIONS

Stephen R.D. Johnston, "Exemestane," *Current Opinion in Oncologic, Endocrine, & Metabolic Investiogatioanal Drugs* (1999) 1(5): 560-572; Abstract.
Chou et al., *Proc. Natl. Acad. Sci. USA*, 1998, 95, 15798-15802, "Desoxyepothilone B is curative against human tumor xenografts that are refractory to paclitaxel".
Demario et al., *J. Clinical Oncology*, 1998, 16 (7), 2557-2567, "Oral Chemotherapy: Rationale and Future Directions".
Sigma-Aldrich on-line catalog, product P1754, "TWEEN 80" (polyoxyethylenesorbitan monooleate), accessed Oct. 14, 2005.

* cited by examiner

*Primary Examiner*—Shaojia Anna Jiang
*Assistant Examiner*—Michael C. Henry
(74) *Attorney, Agent, or Firm*—Yuan Chao; Gary W. Ashley

(57) ABSTRACT

Formulations comprising one or more epothilones together with a pharmaceutically acceptable carrier, in particular such pharmaceutical compositions suitable for oral administration of an epothilone.

11 Claims, No Drawings

THERAPEUTIC FORMULATIONS

CROSS REFERENCE TO RELATED APPLICATIONS

This application claims priority under 35 U.S.C. 119(e) to U.S. Provisional Applications Ser. No. 60/417,536, filed 9 Oct. 2002, and Ser. No. 60/426,585, filed 14 Nov. 2002, each of which is incorporated herein in its entirety.

FIELD OF THE INVENTION

The present invention relates to the formulation and delivery of therapeutic substances. More particularly, this invention relates to formulations and methods for the treatment of hyperproliferative diseases, especially cancer. The invention has relevance to the arts of pharmacology and medicinal chemistry.

BACKGROUND

The class of polyketides known as epothilones has emerged as a source of potentially therapeutic compounds having modes of action similar to paclitaxel (Bollag, et al. 1995; Service 1996; Winkler and Axelsen 1996; Bollag 1997; Cowden and Paterson 1997). Interest in the epothilones and epothilone analogs has grown with the observations that certain epothilones are active against tumors that have developed resistance to paclitaxel (Harris, et al. 1999a) as well as reduced potential for undesirable side-effects (Muhlradt and Sasse 1997). Among the epothilones and epothilone analogs being investigated for therapeutic efficacy are epothilone B 1 (Oza, et al. 2000) and the semi-synthetic epothilone B analogs, BMS-247550 2, also known as "azaepothilone B" (Colevas, et al. 2001; Lee, et al. 2001; McDaid, et al. 2002; Yamaguchi, et al. 2002), and BMS-310705 3.

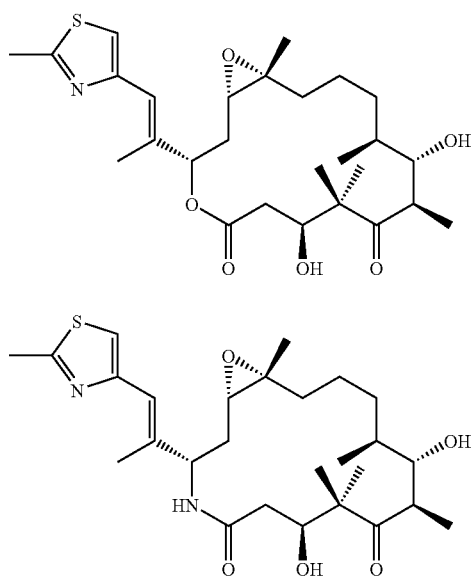

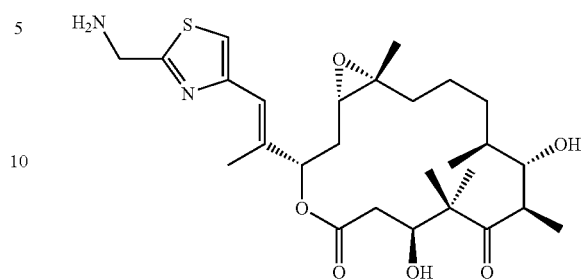

Desoxyepothilone B 4, also known as "epothilone D" is another epothilone derivative having promising anti-tumor properties viz. paclitaxel that is being investigated for therapeutic efficacy (Su, et al. 1997; Chou, et al. 1998a; Chou, et al. 1998b; Harris, et al. 1999b; Chou, et al. 2001; Danishefsky, et al. 2001b; Martin and Thomas 2001; Danishefsky, et al. 2002). This compound has also demonstrated less toxicity than epothilones having 12,13-epoxides, such as epothilone B or BMS-247550, presumably due to the lack of the highly reactive epoxide moiety.

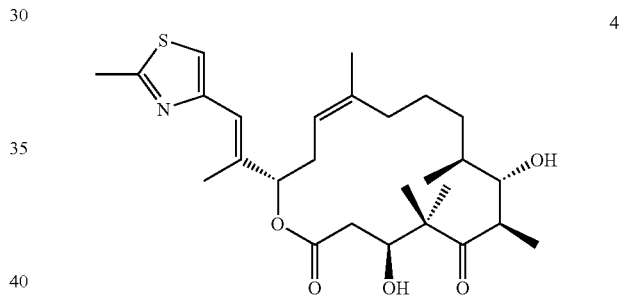

Generally, pharmacologists and physicians prefer therapeutic formulations to have good oral availability to enhance patient compliance and ease of administration (DeMario and Ratain 1998). Formulations showing oral activity in mice have been described for BMS-247550 and BMS-310705 (Lee 2002a; b); however, these compounds lack the structural combination of a lactone oxygen and olefin found with epothilone D.

A single report of a polyethylene glycol-400:ethanol (10:1) formulation of epothilone D delivered orally to one mouse (at a dose of 50 mg/kg) showed no discernable effect on tumor size (Chou, et al. 1998b). Unfortunately, epothilone D has poor aqueous solubility; and current epothilone D formulations include a castor oil derivative solubilizing agent sold under the trade name CREMOPHOR® (BASF Aktiengesellschaft) to enhance solubility. These formulations are suitable only for intravenous delivery. While current epothilone D formulations are acceptable for clinical and therapeutic use, CREMOPHOR® has been associated with patient discomfort and toxicity. CREMAPHOR®-free formulations of epothilone B for intravenous delivery have been described (Van Hoogevest 1999). Therefore, it would be preferable to provide enhanced formulations of epothilone D that do not require CREMOPHOR® and, still more preferably, that can be delivered orally.

SUMMARY OF THE INVENTION

In one aspect, the present invention provides pharmaceutical compositions for treating a hyperproliferative disease, typically, but not necessarily, in a mammal, preferably in a human. In one embodiment, the present invention provides a pharmaceutical composition comprising an epothilone and a pharmaceutically acceptable carrier, embodiments of which carrier will be described in greater detail hereinbelow. The epothilone is provided in a therapeutically effective concentration, and the pharmaceutical composition is effective to deliver a therapeutically effective amount of epothilone by oral administration.

In particular embodiments of the pharmaceutical compositions provided by the invention, the pharmaceutical composition of the invention includes at least one cyclodextrin, and, in more particular embodiments, the cyclodextrin is an hydroxyalkyl-β-cyclodextrin, and, in a still more particular embodiment, an hydroxypropyl-β-cyclodextrin. In other embodiments of the invention, the cyclodextrin is a sulfoalkylcyclodextrin, and in more particular embodiments, the sulfoalkylcyclodextrin is a sulfopropyl-β-cyclodextrin.

In other embodiments of the invention, the epothilone and cyclodextrin are provided in a lyophilized form, which, in some embodiments, is a lyophilate "cake".

In another embodiment, the compounds and compositions of the present invention are used in combination with other therapeutic agents or procedures. In particular embodiments, the other therapeutic agents include other antiproliferative agents, agents that enhance the antiproliferative activity of the antiproliferative compound (e.g., inhibitors of Hsp90), and agents that mitigate undesired side-effects of the antiproliferative agent.

In another aspect of the invention, the pharmaceutical compositions provided are used to treat cancers. In particular embodiments, the compositions comprising an epothilone are used to treat cancers sensitive to epothilones.

In other embodiments, the pharmaceutical compositions provided are used to treat non-cancer diseases characterized by cellular hyperproliferation (e.g., psoriasis, restenosis, multiple sclerosis, rheumatoid arthritis, atherosclerosis, and the like).

In another aspect, the invention provides pharmaceutical compositions effective to provide therapeutically effective dosage levels of an epothilone to a patient in need of such treatment. In particular embodiments, the composition is effective at providing a dosage level between about 1 mg/m$^2$ and about 200 mg/m$^2$.

DETAILED DESCRIPTION OF THE INVENTION

In one aspect, the present invention provides pharmaceutical compositions (also referred to simply as "compositions") for treating a hyperproliferative disease, typically, but not necessarily, in a mammal, preferably in a human. In one embodiment, the present invention provides a pharmaceutical composition comprising an epothilone and a pharmaceutically acceptable carrier, embodiments of which carrier will be described in greater detail hereinbelow. The epothilone is provided in a therapeutically effective concentration, and the pharmaceutical composition is effective to deliver a therapeutically effective amount of epothilone by oral administration. In certain embodiments, the pharmaceutical compositions are provided in a physical form suitable for oral administration, e.g., soft gel caps.

As used herein, the term "epothilone" is used to refer to any epothilone, such as, but are not limited to, epothilone A, epothilone B, epothilone C, epothilone D, epothilone E, epothilone F, 4-desmethylepothilone D, azaepothilone B, 21-aminoepothilone B, 9,10-dehydroepothilone D, 9,10-dehydro-26-trifluoro-epothilone D, 11-hydroxyepothilone D, 19-oxazolylepothilone D, 10,11-dehydro-epothilone D, 19-oxazolyl-10,11-dehydro-epothilone D, 9,10-dehydroepothilone B, 9,10 -dehydroepothilone D, 26-trifluoro-9,10-dehydroepothilone B or D, and analogs and derivatives thereof. The epothilone used in the pharmaceutical compositions of the invention can thus be any epothilone, and, more particularly, any epothilone having useful therapeutic properties (Hoefle, et al. 1993; Nicolaou, et al. 1998; Reichenbach, et al. 1998; Danishefsky, et al. 1999a; Danishefsky, et al. 1999b; Hoefle, et al. 1999; Nicolaou, et al. 1999a; Nicolaou, et al. 1999b; Vite, et al. 1999a; Vite, et al. 1999b; Vite, et al. 1999d; c; Hoefle, et al. 2000a; Hoefle, et al. 2000b; Danishefsky, et al. 2001a; Danishefsky, et al. 2001b; Santi, et al. 2001; Avery 2002; Danishefsky, et al. 2002; Nicolaou, et al. 2002a; Nicolaou, et al. 2002b; Wessjohann and Scheid 2002; White, et al. 2002). Such epothilones can be obtained using any combination of total chemical synthesis, partial chemical synthesis, or chemobiosynthesis methods and materials known to those of skill in organic chemistry, medicinal chemistry, and biotechnology arts (Hoefle, et al. 1993; Hoefle and Kiffe 1997; Hofle and Kiffe 1997; Schinzer, et al. 1997; 1998; Hofle and Sefkow 1998; Mulzer and Mantoulidis 1998; Nicolaou, et al. 1998; Reichenbach, et al. 1998; Schinzer, et al. 1998; Wessjohann and Gabriel 1998; Wessjohann and Kalesse 1998; Altmann, et al. 1999; Danishefsky, et al. 1999a; Danishefsky, et al. 1999b; Hoefle, et al. 1999; Hofmann, et al. 1999; Kim and Borzilleri 1999; Kim and Johnson 1999; Klar, et al. 1999a; b; Mulzer and Mantoulidis 1999; Nicolaou, et al. 1999a; Nicolaou, et al. 1999b; Schupp, et al. 1999; Vite, et al. 1999a; Vite, et al. 1999b; Vite, et al. 1999d; c; Beyer and Mueller 2000; Borzilleri, et al. 2000; Buchmann, et al. 2000; Cabral 2000; Georg, et al. 2000; Gustafsson and Betlach 2000; Hoefle, et al. 2000a; Hoefle, et al. 2000b; Hofle, et al. 2000; Julien, et al. 2000; Kim and Johnson 2000; Li, et al. 2000; Mulzer, et al. 2000; Arslanian, et al. 2001; Danishefsky, et al. 2001 a; Danishefsky, et al. 2001b; Kim and Johnson 2001; Klar, et al. 2001; Kumar, et al. 2001; Lee 2001; Li, et al. 2001); (Mulzer and Martin 2001; Santi, et al. 2001; Strohhaecker 2001; Vite, et al. 2001; Avery 2002; Danishefsky, et al. 2002; Dimarco, et al. 2002; Hoefle and Glaser 2002; Julien, et al. 2002; Khosla and Pfeifer 2002; Koch and Loiseleur 2002; Kuesters and Untemaehrer 2002; Li, et al. 2002; Nicolaou, et al. 2002a; Nicolaou, et al. 2002b; Santi et al. 2002a; Santi, et al. 2002b; Santi et al. 2002c; Smith, et al. 2002; Wessjohann and Scheid 2002; Wessjohann, et al. 2002; White, et al. 2002). Specific examples of epothilones having useful therapeutic properties include, but are not limited to, epothilone A, epothilone B, epothilone C, epothilone D, 4-desmethylepothilone D, azaepothilone B, 21-aminoepothilone B, 9,10-dehydroepothilone D, 9,10-dehydro-26-trifluoro-epothilone D, 11-hydroxyepothilone D, 19-oxazolylepothilone D, 10,11-dehydro-epothilone D, 19-oxazolyl-10,11-dehydro-epothilone D, 9,10-dehydroepothilone B, 9,10-dehydroepothilone D, and analogs and derivatives thereof.

In more particular embodiments of the pharmaceutical compositions provided by the invention, the pharmaceutical composition of the invention includes at least one cyclodextrin. The term "cyclodextrin" as used herein is meant to encompass both native cyclodextrins (e.g., α, β, γ-cyclodextrins and the like) as well as derivatized forms of the native cyclodextrins, such as hydroxyalkylated cyclodextrins (e.g., hydroxyethylated and hydroxypropylated cyclodextrins), sulfoalkylated cyclodextrins (e.g., sulfopropylated and sulfobutylated cyclodextrins), and other chemically derivatized cyclodextrins. In particular embodiments, the cyclodextrin is an hydroxyalkyl-β-cyclodextrin, and, in a still more particular embodiment, an hydroxypropyl-β-cyclodextrin. Still more particular embodiments in which the carrier includes a hydroxypropyl-β-cyclodextrin include those for which the hydroxypropyl-β-cyclodextrin has a degree of substitution of at least about 4.6%, and, more specifically a degree of substitution of at least about 6.5%. Still more specific embodiments of the pharmaceutical composition of the invention are those for which the carrier includes an hydroxypropyl-β-cyclodextrin having a degree of substitution between about 4.6% and about 6.5%. In other embodiments of the invention, the cyclodextrin is a sulfopropyl-β-cyclodextrin.

In one embodiment, the epothilone used in the pharmaceutical composition is epothilone D. In a more specific embodiment, the pharmaceutical composition of the invention comprises epothilone D and an hydroxyalkyl-β-cyclodextrin, and, in a still more particular embodiment, an hydroxypropyl-β-cyclodextrin. In sill more specific embodiments of pharmaceutical compositions comprising epothilone D and an hydroxypropyl-β-cyclodextrin, the hydroxypropyl-β-cyclodextrin has a degree of substitution of at least about 4.6%, and, more specifically, a degree of substitution of at least about 6.5%. Still more specific embodiments of the pharmaceutical composition of the invention are those for which the epothilone is epothilone D and the carrier includes an hydroxypropyl-β-cyclodextrin having a degree of substitution between about 4.6% and about 6.5%. Among the pharmaceutical compositions of the invention including epothilone D and an hydroxypropyl-β-cyclodextrin, more specific embodiments include those for which the epothilone D and the hydroxypropyl-β-cyclodextrin are combined in a weight ratio of about 10 mg epothilone D to about 0.4 g of hydroxypropyl-β-cyclodextrin.

In other embodiments of the invention, the epothilone and cyclodextrin are provided in a lyophilized form, which, in some embodiments, is a lyophilate "cake". Such embodiments can be made using materials and techniques that will be familiar to those having skill in the pharmacy arts (Gennaro 2000). In one particular embodiment, an epothilone and a hydroxyalkyl-βcyclodextrin are combined in an alcohol-water solution that is lyophilized. More specific embodiments include those in which epothilone D and a hydroxypropyl-β-cyclodextrin are combined in a alcohol-water solution that is then lyophilized. In still more particular embodiments, about 10 mg epothilone D and about 0.4 g of hydroxypropyl-β-cyclodextrin are combined in a 60% tert-butanol-water solution that is then lyophilized. In still more specific embodiments, about 10 mg epothilone D and about 0.4 g of hydroxypropyl-β-cyclodextrin are combined in a 60% tert-butanol-water solution and then lyophilized to form a "cake".

Surprisingly, the lyophilates provided by the invention, as described above, have been found to possess useful solubility in pharmaceutically useful carriers, especially pharmaceutically useful carriers that are expected to be better tolerated than carriers comprising CREMAPHOR®. Thus, in another aspect, the present invention provides useful pharmaceutical compositions comprising an epothilone and a hydroxyalkyl-β-cyclodextrin as described above, in a pharmaceutically acceptable carrier that lacks any substantial amount of CREMAPHOR®. More particular embodiments of the present invention include pharmaceutical compositions resulting from the reconstitution of the lyophylate described above using a mixture including water, ethanol, and at least one glycol. As used herein, the term "glycol" is meant to include molecules such as propylene glycol, polyethylene glycol 400, polyoxyethylene sorbitan monooleate (sold under the trade name TWEEN 80), and related oxygenated hydrocarbons. It is understood that glycols of various chain lengths and molecular weights (e.g., polyethylene glycol 1000, other TWEEN compounds) are encompassed within this definition. For therapeutic uses, the water used in the reconstitution mixture is water of a degree of purity that is suitable for injection.

In some embodiments, the mixture used to reconstitute the lyophylate includes water, ethanol and polyoxyethylene sorbitan monooleate (TWEEN 80). In more specific embodiments, the mixture includes at least about 10% water (% v/v), more particularly at least about 40% water (% v/v), and, still more particularly, at least about 60% water (% v/v). In some embodiments, the mixture for reconstitution the lyophylate includes between about 60% water and about 70% water (% v/v), more particularly between about 60% water and about 65% water (% v/v), and, in particular embodiment, about 62.5% water (% v/v).

In some embodiments of the reconstitution mixture having water in the concentrations just described, the mixture further include TWEEN 80 in a concentration between about 25% (% v/v) and about 10% (% v/v), more particularly between about 20% (% v/v) and about 15% (% v/v). In one particular embodiment, TWEEN 80 is provided in a concentration of about 15% (% v/v).

In some embodiments, the reconstitution mixture just described includes a concentration of water and a concentration of TWEEN 80 as just described, with the balance of the mixture being ethanol. Examples of suitable reconstitution mixtures include water/ethanol/TWEEN 80 concentrations (% v/v) of: 10/65/25, 20/55/25, 40/35/25, 62.5/12.5/25, 60/20/20, and 60/25/15. In another embodiment, the reconstitution mixture is propylene glycol/ethanol/water in the ration 40/10/50 (% v/v).

The above-described reconstitution mixtures are suitable for use with any lyophylate formed using any of the combinations of epothilone(s) and a hydroxyalkyl-β-cyclodextrin or sulfoalkyl-β-cyclodextrin described above. More particular embodiments include compositions resulting from the reconstitution of a lyophylate including epothilone D. Still more particular embodiments include those compositions resulting from the reconstitution of a lyophylate for which the epothilone is epothilone D and the hydroxyalkyl-β-cyclodextrin is hydroxypropyl-β-cyclodextrin. Still more particular embodiments include those compositions resulting from the reconstitution of a lyophylate for which the epothilone is epothilone D and the sulfoalkyl-β-cyclodextrin is sulfoypropyl-β-cyclodextrin.

Some embodiments of the invention include compositions resulting from the reconstitution of a lyophylate formed from about 10 mg epothilone D and about 0.4 g of hydroxypropyl-β-cyclodextrin that have been combined in a 60% tert-butanol-water solution, and a reconstitution mixture that includes a water/ethanol/TWEEN 80 combination (% v/v) of: 10/65/25, 20/55/25, 40/35/25, 62.5/12.5/25, 60/20/20, or 60/25/15. In a more specific embodiment, the lyophylate formed from about 10 mg epothilone D and about 0.4 g of hydroxypropyl-β-cyclodextrin that have been combined in a 60% tert-butanol-water solution, and the reconstitution mixture is a water/ethanol/TWEEN 80 combination (% v/v) of: 62.5/12.5/25, 60/20/20, or 60/25/15. A still more specific embodiment is a composition resulting from the reconstitution of a lyophilate formed from about 10 mg epothilone D and about 0.4 g of hydroxypropyl-β-cyclodextrin that have been combined in a 60% tert-butanol-water solution, and a reconstitution mixture that includes a water/ethanol/TWEEN 80 combination (% v/v) of 62.5/12.5/25.

Without wishing to be bound by any particular theory of action, the effectiveness of the combination of a hydroxyalkyl-β-cyclodextrin lyophylate in one of the aqueous reconstitution mixtures described herein to form a therapeutically effective composition is consistent with the formation of an complex between the hydroxyalkyl-β-cyclodextrin and the epothilone in the lyophylate, and, more specifically, an inclusion complex between the hydroxyalkyl-β-cyclodextrin and the epothilone in the lyophylate. Thus, in some embodiments, the present invention includes epothilone D-hydroxypropyl-β-cyclodextrin complexes, and, more specifically, epothilone D-hydroxypropyl-β-cyclodextrin inclusion complexes. The above-described complexes and inclusion complexes can be formed in either the lyophylate and/or the reconstituted solution.

Therapeutic Applications of the Compositions of the Invention

The compositions described herein are effective to deliver a therapeutically effective amount of an epothilone to treat an epothilone-mediated disease, i.e., a disease that responds favorably to the administration of an epothilone to a patient, such as a mammal, and, more particularly, a human, to epothilone administration. Thus, the present invention also includes methods for treating epothilone-mediated diseases. Examples of epothilone-mediated diseases include, but are not limited to, hyperproliferative diseases, such as cancer, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis.

The methods and compositions of the present invention can be used in combination therapies. In other words, the inventive compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved. Thus, the compositions described herein can be combined with other treatment modalities, such as surgery and/or radiation. The compositions described herein can also be used in combination with other oncolytic agents, such a 5-fluorouracil or 5'-deoxy-5-fluoro-N-[(pentyloxy)carbonyl]-cytidine (sold under that trade name ZELODA® (Roche). Illustrative examples of other anti-cancer agents include but are not limited to: (i) alkylating drugs such as mechlorethamine, chlorambucil, Cyclophosphamide, Melphalan, Ifosfamide; (ii) antimetabolites such as methotrexate; (iii) microtubule stabilizing agents such as vinblastin, paclitaxel, docetaxel, and discodermolide; (iv) angiogenesis inhibitors; (v) and cytotoxic antibiotics such as doxorubicin (adriamycin), bleomycin, and mitomycin. Illustrative examples of other anti-cancer procedures include: (i) surgery; (ii) radiotherapy; and (iii) photodynamic therapy.

In another embodiment, the compounds and compositions of the present invention are used in combination with an agent or procedure to mitigate potential side effects from the inventive compound or composition such as diarrhea, nausea and vomiting. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol.

In another aspect of the present invention, the inventive compositions are used to treat non-cancer disorders that are characterized by cellular hyperproliferation. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis. irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

The method of treating such diseases comprises administering a therapeutically effective amount of an inventive compound to a subject suffering therefrom. The method may be repeated as necessary. The inventive methods are described in greater detail below with reference to three illustrative non-cancer disorders.

In one embodiment, the compounds of the present invention are used to treat psoriasis, a condition characterized by the cellular hyperproliferation of keratinocytes which builds up on the skin to form elevated, scaly lesions. The method comprises administering a therapeutically effective amount of an inventive compound to a subject suffering from psoriasis. The method may be repeated as necessary either to decrease the number or severity of lesions or to eliminate the lesions. Clinically, practice of the method will result in a reduction in the size or number of skin lesions, diminution of cutaneous symptoms (pain, burning and bleeding of the affected skin) and/or a reduction in associated symptoms (e.g., joint redness, heat, swelling, diarrhea. abdominal pain). Pathologically, practice of the method will result in at least one of the following: inhibition of keratinocyte proliferation, reduction of skin inflammation (for example, by impacting on: attraction and growth factors, antigen presentation, production of reactive oxygen species and matrix metalloproteinases), and inhibition of dermal angiogenesis.

In another embodiment, the compounds of the present invention are used to treat multiple sclerosis, a condition characterized by progressive demyelination in the brain. Although the exact mechanisms involved in the loss of myelin are not understood, there is an increase in astrocyte proliferation and accumulation in the areas of myelin destruction. At these sites, there is macrophage-like activity and increased protease activity which is at least partially responsible for degradation of the myelin sheath. The method comprises administering a therapeutically effective amount of an inventive compound to a subject suffering from multiple sclerosis. The method may be repeated as necessary to inhibit astrocyte proliferation and/or lessen the severity of the loss of motor function and/or prevent or attenuate chronic progression of the disease. Clinically, practice of the method will result in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically, practice of the method will result in the reduction of one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

In another embodiment, the compositions of the present invention are used to treat rheumatoid arthritis, a multisystem chronic, relapsing, inflammatory disease that sometimes leads to destruction and ankyiosis of affected joints. Rheumatoid arthritis is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and, eventually the pannus grows to fill the joint space. The pannus develops an extensive network of new blood vessels through the process of angiogenesis that is essential to the evolution of the synovitis. Release of digestive enzymes (matrix metalloproteinases (e.g., collagenase, stromelysin)) and other mediators of the inflammatory process (e.g., hydrogen peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint.

In another embodiment, the compositions of the present invention are used to threat atherosclerosis and/or restenosis, particularly in patients whose blockages may be treated with an endovascular stent. Atherosclerosis is a chronic vascular injury in which some of the normal vascular smooth muscle cells ("VSMC") in the artery wall, which ordinarily control vascular tone regulating blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting. Restenosis, the recurrence of stenosis or artery stricture after corrective procedures, is an accelerated form of atherosclerosis. Alternatively, the compositions of the invention can be used to provide a coating comprising a therapeutically effective amount of an epothilone on a stent for and delivering the stent to the diseased artery in a subject suffering from atherosclerosis. Methods for coating a stent with a compound are described for example by U.S. Pat. Nos. 6,156,373 and 6,120, 847. Clinically, practice of the present invention will result in one or more of the following: (i) increased arterial blood flow; (ii) decrease in the severity of clinical signs of the disease; (iii) decrease in the rate of restenosis; or (iv) prevention/attenuation of the chronic progression of atherosclerosis. Pathologically, practice of the present invention will produce at least one of the following at the site of stent implantation: (i) decrease in the inflammatory response, (ii) inhibition of VSMC secretion of matrix metalloproteinases; (iii) inhibition of smooth muscle cell accumulation; and (iv) inhibition of VSMC phenotypic dedifferentiation.

Dosage Levels and Administration

In one embodiment, the compositions of the invention are effective to provide dosage levels of an epothilone, especially epothilone D, or an epothilone selected from the group consisting of: epothilone A, epothilone B, epothilone C, 4-desmethylepothilone D, azaepothilone B, 21-aminoepothilone B, 9,10-dehydroepothilone D, 9,10-dehydro-26-trifluoro-epothilone D, 11-hydroxyepothilone D, 19-oxazolylepothilone D, 10,11-dehydro-epothilone D, 19-oxazolyl- 10,11-dehydro-epothilone D, 9,10-dehydroepothilone B, 9,10-dehydroepothilone D, 26-trifluoro-9,10-dehydoepothilone D, and 26-trifluoro-9,10-dehydoepothilone B, which dosage is to be administered to a subject suffering from cancer or a non-cancer disorder characterized by cellular proliferation are of the order from about 1 mg/m$^2$ to about 200 mg/m$^2$ which may be administered as a bolus (in any suitable route of administration, including oral or intravenous administration) or a continuous infusion (e.g., one hour, three hours, six hours, 24 hours, 48 hours or 72 hours) every week, every two weeks, or every three weeks as needed. It will be understood, however, that the specific dose level for any particular patient depends on a variety of factors. These factors include the activity of the specific compound employed; the age, body weight, general health, sex, and diet of the subject; the time and route of administration and the rate of excretion of the drug; whether a drug combination is employed in the treatment; and the severity of the condition being treated.

In another embodiment, the dosage levels are from about 10 mg/m$^2$ to about 150 mg/m$^2$, preferably from about 10 mg/m$^2$ to about 75 mg/m$^2$ and more preferably from about 15 mg/m$^2$ to about 50 mg/m$^2$ once every three weeks as needed and as tolerated. In another embodiment, the dosage levels are from about 1 mg to about 150 mg/m2, preferably from about 10 mg/m$^2$ to about 75 mg/m$^2$ and more preferably from about 25 mg/m$^2$ to about 50 mg/m$^2$ once every two weeks as needed and as tolerated. In another embodiment, the dosage levels are from about 1 mg/m2 to about 100 mg/m$^2$, preferably from about 5 mg/m$^2$ to about 50 mg/m$^2$ and more preferably from about 10 mg/m$^2$ to about 25 mg/m$^2$ once every week as needed and as tolerated. In another embodiment, the dosage levels are from about 0.1 mg/m$^2$ to about 25 mg/m$^2$, preferably from about 0.5 mg/m$^2$ to about 15 mg/m$^2$ and more preferably from about 1 mg/m$^2$ to about 10 mg/m$^2$ once daily as needed and tolerated.

In order to ensure that toxic limits are not exceeded, side effects are monitored, including peripheral neuropathy, which may manifest itself as numbness in the limbs, dizziness, and the like. Monitoring should begin at some relevant time after infusion; in general, the lower the dosage, the longer the interval between treatment and monitoring. For example, at a dose level of 9 to 60 mg/m$^2$ per infusion monitoring will typically start at day 5 and continue to day 15; however, at higher dosages such as 90 to 120 mg/m$^2$, monitoring should begin the day after infusion is terminated. Other side effects may include nausea and vomiting, fatigue, rash, alopecia, and alteration in vital signs such as orthostatic hypotension. Myelosuppression should also be monitored although myelosuppression is generally not seen with this drug. Myelosuppression may manifest itself as anemia, neutropenia, thrombocytopenia, and the like.

In general, the pharmacokinetics are favorable. Pharmacokinetics are not dose-dependent and the dependence of AUC on dosage was linear from 9 to 150 mg/m$^2$. The half-life of epothilone D has a mean value of 9.6±2.2 hours and a volume of distribution ($V_z$) is 172±74 l, indicating good drug penetration. This is somewhat higher on average than the values for paclitaxel, which are 140±70 l. These pharmacokinetic parameters do not change for a second infusion as compared to a first infusion.

The effectiveness of the drug may be monitored by measuring bundling of microtubules in interphase cells. This is considered a reasonable indicator of effectiveness of microtubule stabilizing agents such as paclitaxel or an epothilone. The bundle formation may readily be measured by immunofluorescence or Western blotting. In a typical determination, whole blood is collected from patients and mononuclear cells (PBMC's) are isolated for evaluation of bundle formation. Substantial amounts of bundle formation are obtained when the dosage is as low as 18 mg/m$^2$ and this increases with dosage. At 120 mg/m$^2$ most of the microtublules are bundled.

EXAMPLES

The following Examples illustrate certain aspects of the present invention to aid those of skill in the art in the art in practicing the invention. The Examples in no way limit the scope of the invention in any manner.

Example 1

Formation of Epothilone D-Hydroxypropyl-β-Cyclodextrin Lyophylate

A combination of ten milligrams ("mg") of epothilone D and 0.4 grams ("g") of hydroxypropyl-β-cyclodextrin ("HPβCD") were dissolved in 60% tert-butanol-water to make 1 milliliter ("mL") of solution. A second solution having ten mg of epothilone D and ten mg of mannitol dissolved in 60% tert-butanol-water was prepared. A third solution of ten mg of epothilone D and ten mg of mannitol in 60% tert-butanol-water was also prepared. Formulation solutions containing ten mg/mL epothilone D were poured into 8 mL glass vials for lyophilization.

Each of the three solutions was freeze-dried using a commercially available lyophilization apparatus to form an excellent lyophilate cake. The cake containing hydroxypropyl-β-cyclodextrin appeared harder and less smooth than the other two cakes.

Example 2

Reconstitution of the Epothilone D-Hydroxypropyl-β-Cyclodextrin Lyophylate and Solubility in Normal Saline The solubilities of the lyophilates made as described in Section 0 were determined for a variety of reconstitution solvents at ambient temperature (i.e., at a temperature between about 20° C. and about 25° C.). Approximately one mg of epothilone D was placed in a glass test tube. Ser. additions of reconstitution solvent to make 100 microliters ("μL")-, 900 μL-, and 9.0 mL-volume solutions were made to the test tube. After each addition of reconstitution composition, the solution was shaken vigorously for thirty seconds. Upon dissolution of the lyophilate, the solubility upon dilution with normal saline was determined.

Only lyophilates made using hydroxypropyl-β-cyclodextrin showed desirable solubilities (i.e., a solubility greater than about one mg/mL). The results for various reconstitution solvents are shown in Table 1. ("Wfl" is water, "PG" is propylene glycol, "EtOH" is ethanol, and "PEG400" is polyethylene glycol 400. The symbol "D" indicates dissolution; the letter "P" indicates precipitation.)

TABLE 1

| Reconstitution Solvent(% v/v) | Solubility S (mg/mL) | Solubility After Dilution with Normal Saline 1:10/1:20/1:100 |
|---|---|---|
| Wfl/EtOH/Tween 80 | | |
| 10/65/25 | 1 ≦ S < 10 | D// |
| 20/55/25 | 1 ≦ S < 10 | D// |
| 40/35/25 | 1 ≦ S < 10 | D// |
| 62.5/12.5/25 | 1 ≦ S < 10 | D// |
| 60/20/20 | 2 ≦ S < 10 | D/D/ |
| 60/25/15 | S ≧ 10 | D/D/D |
| 60/35/5 | S ≧ 10 | P// |
| PG/EtOH/Wfl | | |
| 40/10/50 | 0.1 ≦ S < 1.0 | D// |

The results indicate the best results are achieved with the three-component solvent system: Wfl/EtOH/Tween 80=60/25/15 (% v/v), which could be diluted in normal saline as much as 100-fold without precipitation. Compositions for which the amount of Tween 80 was more than about 20% by volume, or less than about 10% by volume, showed less favorable dilution performance.

Example 3

Oral Activity of Epothilone D

Three test groups, each of five rats, received either an i.v. dose of epothilone D (10 mg/kg), an oral dose of epothilone D at 20 mg/kg, or an oral dose of epothilone D at 40 mg/kg. Blood samples were collected from the rats over a 24-hour period following dosing. The absolute bioavailability at the 20 mg/kg and 40 mg/kg oral doses ranged from 7–10% and 10–20%, respectively. The half-life was 8 hours for the i.v. group snf 5.6–6 hours for the oral groups. As expected, Cmax was significantly higher and clearance was faster with i.v. dosing.

In a similar study, three beagle dogs received a single 2 mg/kg i.v. dose of epothilone D followed at one week intervals by a 2 mg/kg and 4 mg/kg oral dose of epothilone D administered by gavage in the same vehicle as i.v. dosing (30% propylene glycol, 20% Chremophor®, and 50% ethanol) diluted 1:10. Blood samples were collected pre-dose, at the end of infusion, or immediately post-dose following oral administration through 48 hours post-dose. Hetamology and blood chemistries were monitored to ensure animals had recovered prior to each dose. Dogs receiving i.v. epothilone D experienced significant hypersensitivity reactions, but oral dosing was well-tolerated.

Plasma samples from the dogs were analyzed using an LC/MS/MS assay validated over a range of 2 ng/mL–500 ng/mL, and the data was analyzed using Kinetica version 4.1.1 (InnaPhase Corporation, Philadelphia, Pa.). Pharmacokinetic parameters were calculated using non-compartmental analysis and modeled using a two-compartment extravascular model. The calculated AUC for the 2 mg/kg and 4 mg/kg oral doses were 9,856±3,879 ng*h/mL and 15,486±8,060 ng*h/mL respectively, and the oral bioavailability was >50%. The average half-life with oral dosing was 9.13 hours with the half-life somewhat longer with the 4 mg/kg dose (10.9 hours versus 6.4 hours for the 2 mg/kg dose). The average clearance with oral dosing was 0.27 L/h/kg, $V_{ss}$=2.57 L/kg, and MRT=9.81 hours. Clearance, $V_{ss}$, MRT, and half-life were essentially the same as observed with i.v. dosing.

These data demonstrate that epothilone D has good oral bioavailability, suggesting that oral administration to cancer patients or patients suffereing from other hyperproliferative conditions or diseases is feasible.

BIBLIOGRAPHY

The following references are incorporated herein by reference in their entirety and for all purposes.

(1998). Ger. Offen. DE 19821954.

Altmann, K.-h., Bauer, A., et al. (1999). PCT Int. Appl. WO 9959985.

Arslanian, R. L., Ashley, G., et al. (2001). PCT Int. Appl. WO 0183800.

Avery, M. A. (2002). PCT Int. Appl. WO 0230356.

Beyer, S. and Mueller, R.-J. (2000). Ger. Offen. DE 19846493.

Bollag, D. M. (1997). "Epothilones: novel microtubule-stabilizing agents." *Expert Opinion on Investigational Drugs* 6(7): 867–873.

Bollag, D. M., McQueney, P. A., et al. (1995). "Epothilones, a new class of microtubule-stabilizing agents with a taxol-like mechanism of action." *Cancer Res* 55(11): 2325–33.

Borzilleri, R. M., Kim, S.-H., et al. (2000). PCT Int. Appl. WO 0057874.

Buchmann, B., Klar, U., et al. (2000). PCT Int. Appl. WO 0000485.

Cabral, F. (2000). PCT Int. Appl. WO 0071752.

Chou, T.-C., O'Connor, O. A., et al. (2001). "The synthesis, discovery, and development of a highly promising class of microtubule stabilization agents: curative effects of desoxyepothilones B and F against human tumor xenografts in nude mice." *Proceedings of the National Academy of Sciences of the United States of America* 98(14): 8113–8118.

Chou, T. C., Zhang, X. G., et al. (1998a). "Desoxyepothilone B is curative against human tumor xenografts that are refractory to paclitaxel." *Proc Natl Acad Sci USA* 95(26): 15798–802.

Chou, T.-C., Zhang, X.-G., et al. (1998b). "Desoxyepothilone B is curative against human tumor xenografts that are refractory to paclitaxel." *Proceedings of the National Academy of Sciences of the United States of America* 95(26): 15798–15802.

Colevas, A. D., West, P. J., et al. (2001). "Clinical trials referral resource. Current clinical trials of epothilone B analog (BMS-247550)." *Oncology (Huntingt)* 15(9): 1168–9, 1172–5.

Cowden, C. J. and Paterson, I. (1997). "Synthetic chemistry. Cancer drugs better than taxol?" *Nature* 387(6630): 238–9.

Danishefsky, S. J., Balog, A., et al. (1999a). PCT Int. Appl. WO 9943653.

Danishefsky, S. J., Balog, A., et al. (1999b). PCT Int. Appl. WO 9901124.

Danishefsky, S. J., Bertinato, P., et al. (2001a). U.S. Pat. No. 6,204,388.

Danishefsky, S. J., Lee, C. B., et al. (2001b). PCT Int. Appl. WO 0164650.

Danishefsky, S. J., Stachel, S. J., et al. (2002). U.S. Pat. Appl. Publ. 20020058286.

DeMario, M. D. and Ratain, M. J. (1998). "Oral Chemotherapy: Rationale and Future Directions." *J Clin Oncol* 16(8): 2557–2567.

Dimarco, J. D., Gougoutas, J. Z., et al. (2002). PCT Int. Appl. WO 0214323.

Gennaro, A. R., Ed. (2000). *Remington: The Science and Practice of Pharmacy*. Philadelphia, Lipincott Williams & Wilkins.

Georg, G. I., Nair, S. K., et al. (2000). PCT Int. Appl. WO 0058254 .

Gustafsson, C. and Betlach, M. C. (2000). U.S. Pat. No. 6,090,601.

Harris, C. R., Balog, A., et al. (1999a). "Epothilones: microtubule stabilizing agents with enhanced activity against multidrug-resistant cell lines and tumors." *Actualites DE Chimie Therapeutique* 25: 187–206.

Harris, C. R., Kuduk, S. D., et al. (1999b). "New Chemical Synthesis of the Promising Cancer Chemotherapeutic Agent 12,13-Desoxyepothilone B: Discovery of a Surprising Long-Range Effect on the Diastereoselectivity of an Aldol Condensation." *Journal of the American Chemical Society* 121(30): 7050–7062.

Hoefle, G., Bedorf, N., et al. (1993). Ger. Offen. DE 4138042.

Hoefle, G. and Glaser, N. (2002). PCT Int. Appl. WO 0224712.

Hoefle, G., Glaser, N., et al. (2000a). Ger. Offen. DE 19907588.

Hoefle, G., Glaser, N., et al. (2000b). PCT Int. Appl. WO 0050423.

Hoefle, G. and Kiffe, M. (1997). Ger. Offen. DE 19542986.

Hoefle, G., Reichenbach, H., et al. (1999). PCT Int. Appl. WO 9965913.

Hofle, G., Glaser, N., et al. (2000). Eur. Pat. Appl. Ep 987268.

Hofle, G. and Kiffe, M. (1997). PCT Int. Appl. WO 9719086.

Hofle, G. and Sefkow, M. (1998). PCT Int. Appl. WO 9838192.

Hofmann, H., Mahnke, M., et al. (1999). PCT Int. Appl. WO 9942602.

Julien, B., Katz, L., et al. (2002). U.S. Pat. No. 6,410,301.

Julien, B., Katz, L., et al. (2000). PCT Int. Appl. WO 0031247.

Khosla, C. and Pfeifer, B. (2002). PCT Int. Appl. WO 0268613.

Kim, S.-H. and Borzilleri, R. M. (1999). PCT Int. Appl. WO 9927890.

Kim, S.-H. and Johnson, J. A. (1999). PCT Int. Appl. WO 9928324.

Kim, S.-H. and Johnson, J. A. (2000). PCT Int. Appl. WO 0071521.

Kim, S.-h. and Johnson, J. A. (2001). U.S. Pat. No. 6,320,045.

Klar, U., Gay, J., et al. (2001). PCT Int. Appl. WO 0166154.

Klar, U., Schwede, W., et al. (1999a). Ger. Offen. DE 19735575.

Klar, U., Schwede, W., et al. (1999b). Ger. Offen. DE 19735574.

Koch, G. and Loiseleur, O. (2002). PCT Int. Appl. WO 0257251.

Kuesters, E. and Unternaehrer, H. (2002). PCT Int. Appl. WO 0246196.

Kumar, A. M., Klein, J. P., et al. (2001). PCT Int. Appl. WO 0126693.

Lee, F. Y. (2001). PCT Int. Appl. WO 0172721.

Lee, F. Y., Borzilleri, R., et al. (2001). "BMS-247550: a novel epothilone analog with a mode of action similar to paclitaxel but possessing superior antitumor efficacy." *Clin Cancer Res* 7(5): 1429–37.

Lee, F. Y. F. (2002a). PCT Int. Appl. WO 0266033.

Lee, F. Y. F. (2002b). PCT Int. Appl. WO 0266038.

Li, W., Matson, J. A., et al. (2000). PCT Int. Appl. WO 0039276.

Li, W.-s., Thornton, J. E., et al. (2002). PCT Int. Appl. WO 0260904.

Li, W. S., Thornton, J. E., et al. (2001). PCT Int. Appl. WO 0170716.

Martin, N. and Thomas, E. J. (2001). "Total syntheses of epothilones B and D: applications of allylstannanes in organic synthesis." *Tetrahedron Letters* 42(47): 8373–8377.

McDaid, H. M., Mani, S., et al. (2002). "Validation of the Pharmacodynamics of BMS-247550, an Analogue of Epothilone B, during a Phase I Clinical Study." *Clin Cancer Res* 8(7): 2035–43.

Muhlradt, P. F. and Sasse, F. (1997). "Epothilone B stabilizes microtubuli of macrophages like taxol without showing taxol-like endotoxin activity." *Cancer Res* 57(16): 3344–6.

Mulzer, J. and Mantoulidis, A. (1998). Ger. Offen. DE 19726627.

Mulzer, J. and Mantoulidis, A. (1999). PCT Int. Appl. WO 9903848.

Mulzer, J., Mantoulidis, A., et al. (2000). Ger. Offen. DE 19848306.

Mulzer, J. and Martin, H. (2001). PCT Int. Appl. WO 0107439.

Nicolaou, C. K., He, Y., et al. (1998). PCT Int. Appl. WO 9825929.

Nicolaou, K. C., He, Y., et al. (2002a). U.S. Pat. No. 6,441,186.

Nicolaou, K. C., Hepworth, D., et al. (1999a). PCT Int. Appl. WO 9967253.

Nicolaou, K. C., King, N. P., et al. (2002b). U.S. Pat. No. 6,380,394.

Nicolaou, K. C., King, N. P., et al. (1999b). PCT Int. Appl. WO 9967252.

Oza, A., Zamek, R. M., et al. (2000). "A phase I and pharmacologic trial of weekly epothilone B in patients with advanced malignancies." *Annals of Oncology* 11 (Suppl.4): 133.

Reichenbach, H., Hofle, G., et al. (1998). PCT Int. Appl. WO 9822461.

Santi, D., Ashley, G., et al. (2002a). U.S. Pat. Appl. Publ. 20020052028.

Santi, D., Fardis, M., et al. (2001). PCT Int. Appl. WO 0192255.

Santi, D., Metcalf, B., et al. (2002b). PCT Int. Appl. WO 0208440.

Santi, D. V., Ashley, G., et al. (2002c). PCT Int. Appl. WO 0212534.

Schinzer, D., Limberg, A., et al. (1997). Ger. DE 19636343.

Schinzer, D., Limberg, A., et al (1998). PCT Int. Appl. WO 9808849.

Schupp, T., Ligon, J. M., et al. (1999). PCT Int. Appl. WO 9966028.

Service, R. F. (1996). "Tumor-killer made; how does it work?" *Science* 274(5295): 2009.

Smith, A. B., Beauchamp, T. J., et al. (2002). U.S. Pat. Appl. Publ. 20020103387.

Strohhaecker, J. (2001). PCT Int. Appl. WO 0160976.

Su, D.-S., Meng, D., et al. (1997). "Total synthesis of (-)-epothilone B: an extension of the Suzuki coupling method and insights into structure-activity relationships of the epothilones." *Angewandte Chemie, International Edition in English* 36(7): 757–759.

Van Hoogevest, P. (1999). PCT Int. Appl. WO 9939694.

Vite, G. D., Borzilleri, R. M., et al. (1999a). PCT Int. Appl. WO 9954330.

Vite, G. D., Borzilleri, R. M., et al. (1999b). PCT Int. Appl. WO 9902514.

Vite, G. D., Kim, S.-H., et al. (2001). PCT Int. Appl. WO 0173103.

Vite, G. D., Kim, S.-H. K., et al. (1999c). PCT Int. Appl. WO 9954318.

Vite, G. D., Kim, S.-H. K., et al. (1999d). PCT Int. Appl. WO 9954319.

Wessjohann, L. A. and Gabriel, T. (1998). Ger. Offen. DE 19701758.

Wessjohann, L. A. and Kalesse, M. (1998). Ger. Offen. DE 19713970.

Wessjohann, L. A. and Scheid, G. (2002). Ger. Offen. DE 10051136.

Wessjohann, L. A., Scheid, G., et al. (2002). PCT Int. Appl. WO 0232844.

White, J. D., Carter, R. G., et al (2002). U.S. Pat. Appl. Publ. 20020062030.

Winkler, J. D. and Axelsen, P. H. (1996). "A model for the taxol (paclitaxel)/epothilone pharmacophore." *Bioorganic & Medicinal Chemistry Letters* 6(24): 2963–2966.

Yamaguchi, H., Paranawithana, S. R., et al (2002). "Epothilone B analogue (BMS-247550)-mediated cytotoxicity through induction of Bax conformational change in human breast cancer cells." *Cancer Res* 62(2): 466–71.

What is claimed is:

1. A pharmaceutical composition comprising an epothilone together with a pharmaceutically acceptable carrier comprising 10 to 62.5% v/v water, 12.5 to 65% v/v ethanol, and 10 to 25% v/v polyoxyethylene sorbitan monooleate, wherein the composition comprises at least one cyclodextrin, and wherein the epothilone is provided at a dosage level between about 1 mg/m$^2$ and about 200 mg/m$^2$.

2. The pharmaceutical composition of claim 1, wherein the cyclodextrin is selected from the group consisting of β-cyclodextrin, hydroxypropyl-β-cyclodextrin, and sulfopropyl-β-cyclodextrin.

3. The pharmaceutical composition of claim 2, wherein the epothilone is selected from the group consisting of epothilone D, epothilone B, 9,10-dehydro-epothilone D, and 9,10-dehydro-epothilone B.

4. The pharmaceutical composition of claim 3, wherein the epothilone is epothilone D.

5. The pharmaceutical composition of claim 4, wherein the cyclodextrin is hydroxypropyl-β-cyclodextrin.

6. The pharmaceutical composition of claim 5, wherein the cyclodextrin is sulfopropyl-β-cyclodextrin.

7. A method of preparing a pharmaceutical composition, said method comprising the steps of obtaining a lyophilate comprising an epothilone and a cyclodextrin; and dissolving said lyophilate in a reconstitution solvent comprising 10 to 62.5% v/v water, 12.5 to 65% v/v ethanol, and 10 to 25% v/v polyoxyethylene sorbitan monooleate.

8. The method of claim 7, wherein the reconstitution solvent comprises between about 15 and about 20% v/v polyoxyethylene sorbitan monooleate.

9. A soft gel cap comprising a pharmaceutical composition of claim 1.

10. The pharmaceutical composition of claim 1, wherein the epothilone is provided at a dosage level between about 10 mg/m$^2$ and about 150 mg/m$^2$.

11. The pharmaceutical composition of claim 1, wherein the epothilone is provided at a dosage level between about 15 mg/m$^2$ and about 50 mg/m$^2$.

* * * * *